(12) United States Patent
Harrison et al.

(10) Patent No.: US 7,664,658 B2
(45) Date of Patent: Feb. 16, 2010

(54) METHOD FOR ENABLING OR BLOCKING AN OPERATING MODE OF A MEDICAL DIAGNOSTIC DEVICE

(75) Inventors: Sean Harrison, Weisendorf (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 962 days.

(21) Appl. No.: 11/089,248

(22) Filed: Mar. 24, 2005

(65) Prior Publication Data

US 2005/0215880 A1    Sep. 29, 2005

(30) Foreign Application Priority Data

Mar. 25, 2004    (DE) .................. 10 2004 014 712

(51) Int. Cl.
*G06K 7/00*    (2006.01)

(52) U.S. Cl. ................ 705/2; 705/3; 600/300; 235/462.46; 235/491; 235/375

(58) Field of Classification Search ................ 705/2–3; 600/300; 235/462.4, 491, 375
See application file for complete search history.

(56) References Cited

U.S. PATENT DOCUMENTS

| | | | |
|---|---|---|---|
| 4,857,716 A | 8/1989 | Gombrich et al. | |
| 5,567,415 A * | 10/1996 | Porter | 424/9.52 |
| 5,636,259 A * | 6/1997 | Khutoryansky et al. | 378/197 |
| 6,092,722 A | 7/2000 | Heinrichs et al. | |
| 6,099,178 A * | 8/2000 | Spurr et al. | 400/207 |
| 6,167,297 A * | 12/2000 | Benaron | 600/431 |
| 6,172,764 B1 * | 1/2001 | Shoki | 358/1.15 |
| 6,360,174 B1 * | 3/2002 | Shoki | 702/55 |
| 6,436,032 B1 | 8/2002 | Eto et al. | |
| 6,658,219 B1 * | 12/2003 | Ito et al. | 399/27 |
| 6,817,693 B2 * | 11/2004 | Phillips et al. | 347/19 |
| 2001/0011336 A1 * | 8/2001 | Sitka et al. | 711/161 |
| 2003/0023460 A1 * | 1/2003 | Ackermann et al. | 705/2 |
| 2003/0110260 A1 | 6/2003 | Kuth et al. | |
| 2005/0052661 A1 * | 3/2005 | Lapstun et al. | 358/1.1 |

FOREIGN PATENT DOCUMENTS

| | | |
|---|---|---|
| DE | 297 14 826 U1 | 2/1999 |
| DE | 100 14 542 A1 | 10/2001 |
| WO | WO 03/094090 A2 | 11/2003 |

* cited by examiner

*Primary Examiner*—Gerald J. O'Connor
*Assistant Examiner*—Sind Phongsvirajati

(57) ABSTRACT

A method for the enabling or blocking of an operating mode in a medical diagnostic device enables the operating mode of the diagnostic device only after successful verification of the consumable material required for the operational mode. The consumable material is identified by a machine-readable identification tag, which is read off by a reading device.

7 Claims, 2 Drawing Sheets

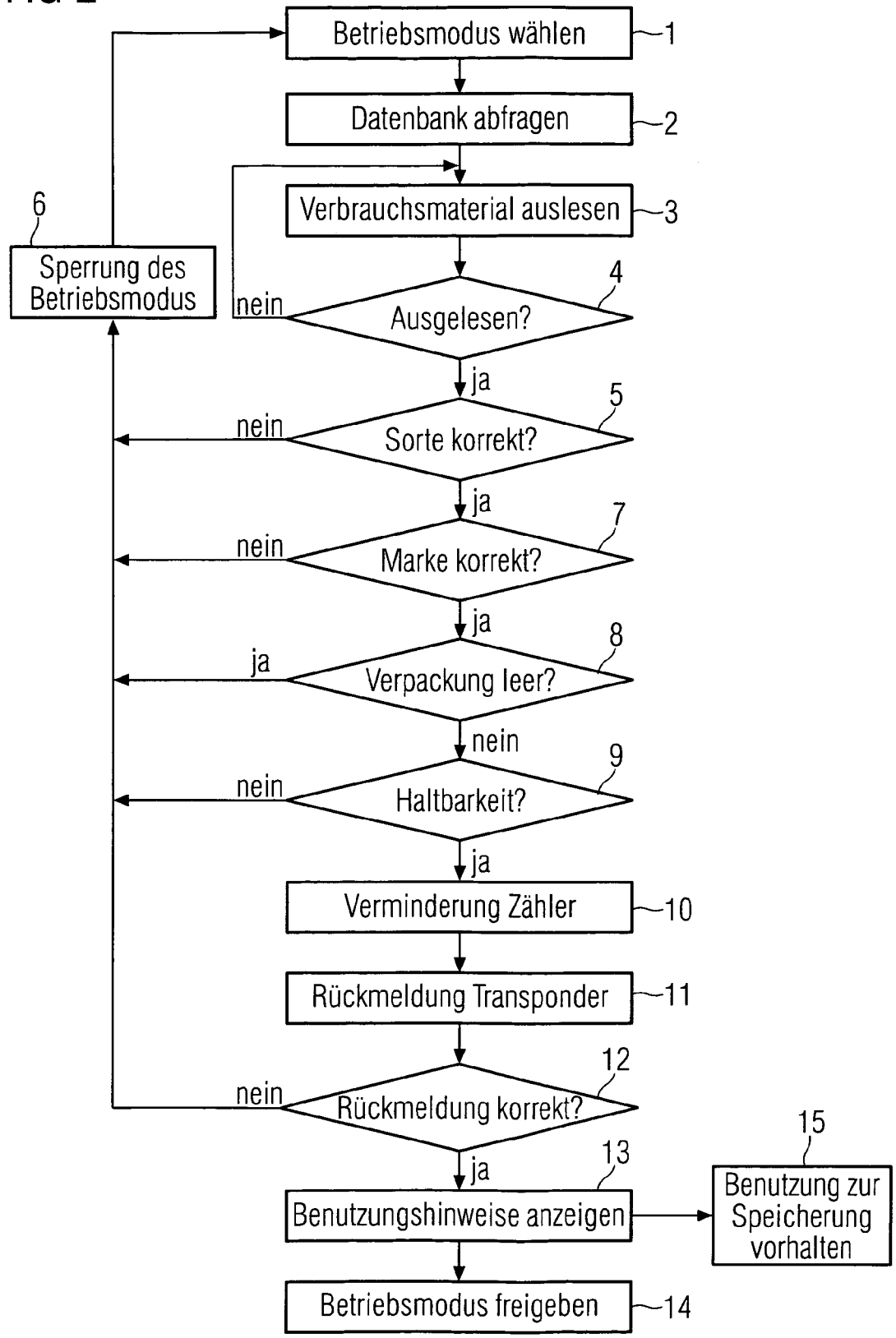

METHOD FOR ENABLING OR BLOCKING AN OPERATING MODE OF A MEDICAL DIAGNOSTIC DEVICE

CROSS REFERENCE TO RELATED APPLICATIONS

This application claims priority to the German application No. 10 2004 014 712.4, filed Mar. 25, 2004 which is incorporated by reference herein in its entirety.

FIELD OF INVENTION

The present invention relates to a method for the enabling or blocking of an operating mode in a medical diagnostic device, in particular to image-generating diagnostics.

BACKGROUND OF INVENTION

Such a method is known from DE 102 20 348 A1. Whenever a user wishes to use a piece of medical equipment, a check is made as to whether the user is authorized to use said equipment and whether the costs incurred are to be paid before the use thereof. Use is automatically enabled if authorization still exists, and if no costs are outstanding. Alternatively, use is automatically blocked if authorization no longer exists, or if costs are still outstanding.

DE 101 55 092 A1 discloses a method for enabling an operational part of a computer software product and of installations pertaining thereto. As soon as a user wishes to use the operational part of the computer software product, a processor causes a transmitter to transmit a launch signal. It is only when a transponder receives this launch signal and thereupon transmits back an enabling code that the operational part of the computer software product is run.

SUMMARY OF INVENTION

In medical diagnostic devices, in particular for image-generating diagnostics, consumable materials are frequently used. These may be, for example, sedatives or contrast media. In particular, when using contrast media in image-generating diagnostics, for example in computer tomography scanners or magnetic resonance tomography scanners, correct use is necessary. Likewise the possibility should be excluded of a contrast medium or consumable material that is incompatible with the respective selected operating mode of the diagnostic device being used.

An object of the present invention is to provide a method by means of which the use in medical diagnostic devices of consumable materials that are not suitable for the respective operating mode is prevented.

The above object is achieved by the claims. The consumable materials required for an operating mode are provided with a machine-readable identification tag and are detected by a reading device. Then an enabling system connected to the reading device verifies that the consumable materials required have been detected correctly by interrogating a database connected thereto which stores corresponding information relating to the respective operating mode. It is only after successful verification of the consumable material that the enabling system releases the operating mode of the diagnostic device. If, for example, a user inadvertently attempts to use an incorrect contrast medium for an examination, this is detected by the enabling system and the respective operating mode is blocked. Unnecessary repeat examinations are thus avoided, which is an advantage in particular where there may be side effects of using consumable materials or of the examination itself, for example in computer tomography scanning.

In an advantageously designed method, each time the identity tag is read off, the reading device decreases a value on a counter located in the identification tag by a given value. Here the counter contains the possible number of applications for the respective pack of consumable material. The enabling system releases the operating mode of the diagnostic device only when the decrease on the counter has been successfully verified. As soon as the counter reaches a given value, the operating mode of the diagnostic device is blocked by the enabling system when the identification tag is read off by the reading device. This prevents, for example, a used bottle of contrast medium being filled with a contrast medium that does not correspond with the operating mode and being incorrectly used.

In an advantageously designed method, the enabling system releases the operating mode of the diagnostic device only after successful verification by the reading device of a particular manufacturer of the required consumable material. This has the advantage, in particular when using contrast media in image-generating diagnostics, that the same contrast medium from a particular manufacturer is always used and that no generic products of a different quality or composition come into use, in which case the parameters of the examination would have to be modified.

In an advantageously designed method, the use of the consumable material is transmitted by the enabling system to a storage device that is connected to the diagnostic device, such that the use can be stored in a patient-related manner. This has the advantage that the costs of medical diagnostic examination can be calculated in a patient-related manner. There is the additional advantage that the use of the consumable material is documented in a patient-related manner, which is particularly desirable where the consumable material has side effects.

In a further advantageously designed method, the database likewise stores advice on the use of the respective operating mode and in particular on the consumable material used. After the consumable material has been read in by the reading device, information on the use of the consumable material in the respective operating mode of the diagnostic device is requested from the database by the enabling system and displayed on a display medium together with advice relating to the use of the respective mode of operation. This minimizes the risk of incorrect operation by the user.

One embodiment of the method is advantageous in that a contactlessly readable transponder is read off by the reading device, as a result of which handling is facilitated.

BRIEF DESCRIPTION OF THE DRAWINGS

Further advantages and details will become apparent from the description that follows of an embodiment, in conjunction with the drawings. The drawings show:

FIG. 2: a flowchart showing the main process steps.

DETAILED DESCRIPTION OF INVENTION

Figure 1:
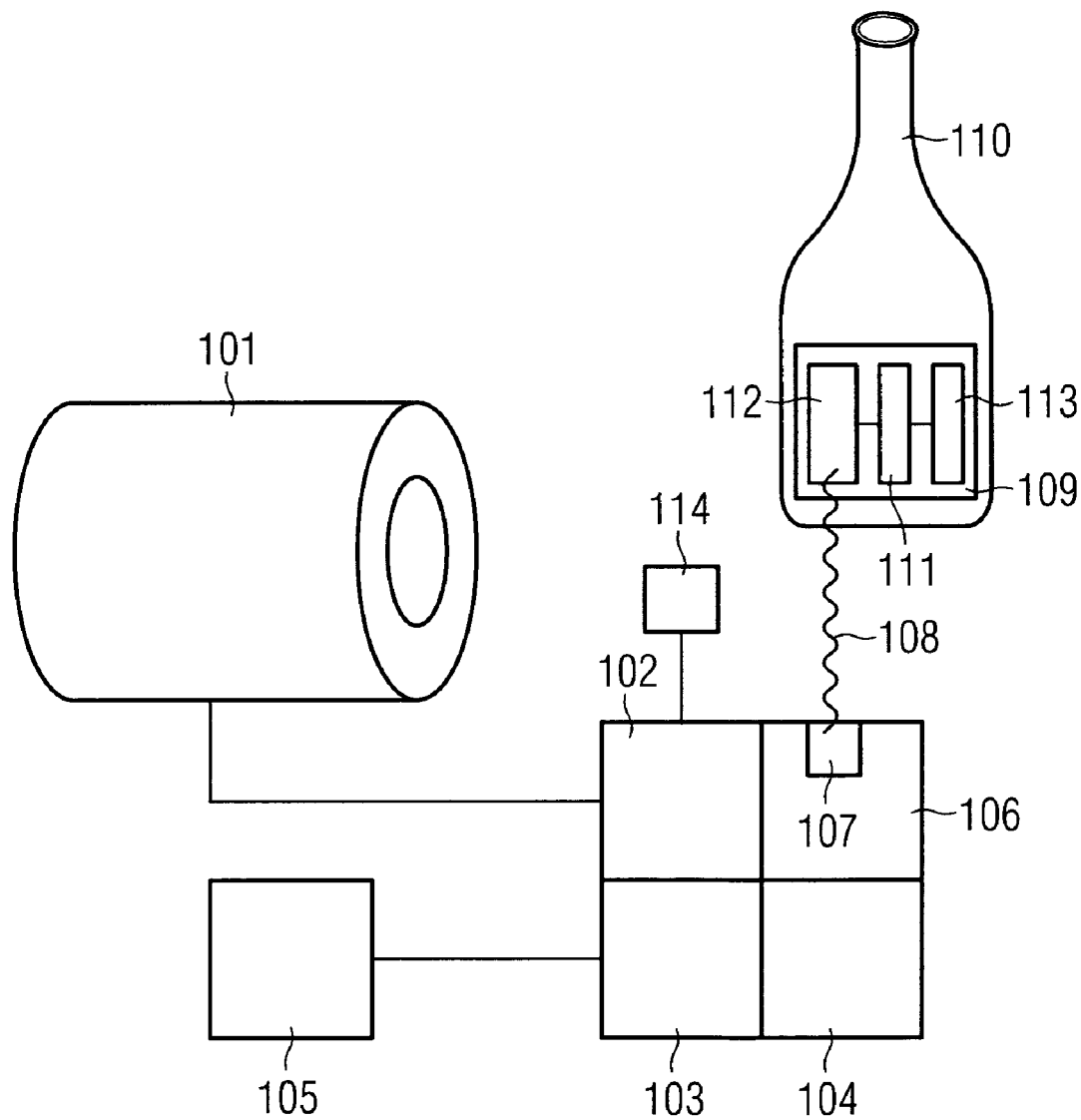
FIG. 1: a diagram of the diagnostic device.

The diagnostic device shown in diagram form in FIG. 1 comprises a diagnostic module 101, which is connected to an enabling system 102. The test control unit 103 is used to select an operating mode for the diagnostic device. A database 104 stores information relating to the respective mode of operation, which information is interrogated by the enabling system 102. In particular, information relating to the consumable material required for the respective operating mode is interrogated and displayed on a display medium 105. A reading device 106 that is connected to said enabling system comprises a transmitter and receiver unit 107, which establishes a wireless communication 108 with a transponder 109. The transponder 109 is affixed to a pack of consumable material, which here takes the form of a bottle of contrast medium 110. In addition to an operating unit 111 and a transmitter and receiver unit 112, the transponder 109 also contains a memory in the form of an EEPROM 113. Said EEPROM 113 is both readable and writable by the operating unit 111. Writing procedures, that is, changes to the EEPROM 113 are irreversible. The EEPROM 113 functions as a counter that stores the number of possible uses of the bottle of contrast medium 110. In each read-off procedure, the operating unit 111 transmits the value stored in the EEPROM 113 to the reading device 106 and decreases the value stored in the EEPROM by "one". A successful or unsuccessful decrease is likewise transmitted to the reading device 106. The EEPROM 113 additionally contains information on the brand and "best before" date of the contrast medium. The above data are likewise transmitted to the reading device 106. All the data transmitted by the transponder to the reading device 106 are further transmitted to the enabling system 102, which decides from data whether it will enable or block the operating mode of the diagnostic device. If, for example, the "best before" date on the contrast medium has been exceeded, the operating mode of the diagnostic device is blocked. Likewise from a given value of the EEPROM 113, preferably the value "zero", the operating mode of the diagnostic device is blocked by the enabling system 102 and thus the bottle of contrast medium 110 cannot be used. As a result thereof, use of a bottle of contrast medium 110 filled with a potentially inferior generic product is prevented, for example. After successful verification by the reading device 106, the enabling system 102 transmits the use of the consumable material to a connected memory unit 114, wherein corresponding data are stored in a patient-related manner.

According to the method shown in FIG. 2, the operating mode of the diagnostic device is selected in step 1. Then in step 2 information from the database relating to the operating mode is interrogated and stored in the enabling system. Said information contains in particular the consumable material that is required for the respective mode of operation. In step 3 the user is prompted to determine, by means of the reading device, the consumable material that is required for the mode of operation. In step 4 a check is made as to whether the consumable material has been determined. If this is not the case, the user is again prompted to do so in step 3. If the consumable material is detected, then a check is made in step 5 as to whether the correct consumable material has been detected. If this is not the case, in step 6, the operating mode is blocked and the user is again prompted in step 1 to select a mode of operation. In three subsequent steps 7, 8 and 9, the manufacturer of the consumable material, the number of applications that can be carried out with the respective pack and the "best before" date are checked. If one of the checks 7, 8 or 9 is unsuccessful, in step 6 the operating mode is blocked and the user is again prompted in step 1 to select an operating mode. Where there is a positive outcome for selection steps 7, 8 and 9, in the subsequent step 10 the number on the consumable material counter in the transponder is decreased by the value "one". In step 11 the transponder subsequently provides notification as to whether the decrease in the number on the counter has been successfully achieved. In step 12, the enabling system checks from the data transmitted by the transponder whether the decrease in the number on the counter was successful. If this is not the case, the operating mode is blocked in step 6 and the user is again prompted in step 1 to select an operating mode. In the case of a correct decrease in the number on the counter, in step 13 the advice relating to the use of the consumable material and operational mode that has been interrogated in the database is displayed on the display medium. The operating mode is then enabled in step 14 and the use of the consumable material is stored in step 15 at the same time as the patient-related documentation.

The invention claimed is:

1. A method of enabling or blocking an operating mode of a medical diagnostic device comprising an enabling system for enabling or blocking the operating mode, a reading device and a database, the enabling system connected to the reading device and the database, and the database comprising stored information related to a plurality of operating modes and to consumable materials required for executing medical procedures corresponding to the operating modes, the method comprising:

(a) reading by means of the reading device an identification tag affixed to a consumable material, the identification tag denoting consumable material required for executing a specific medical procedure corresponding to a specific operating mode, wherein the identification tag denotes a type of the consumable material, a manufacturer of the consumable material, a "best before" date of the consumable material, and wherein the identification tag further comprises a counter having a value of a remaining number of uses of the consumable material;

(b) verifying the denoted consumable material, by means of the enabling system by (i) verifying the denoted consumable material matches the consumable-material-related information stored in the database corresponding to the specific operating mode as to both type and manufacturer, (ii) verifying the value of the remaining number of uses of the consumable material has not reached a given value, (iii) verifying the "best before" date of the consumable material has not been exceeded, and (iv) decreasing the value in the counter by a specified value, and verifying the counter is successfully decreased; and (c) enabling the specific operating mode by means of the enabling system and transmitting data corresponding to use of the consumable material to be stored in a patient-related manner only if all of steps (i), (ii), (iii) and (iv) are verified, otherwise blocking the specific operating mode.

2. The method according to claim 1, wherein the medical diagnostic device is a medical imaging device.

3. The method according to claim 1, wherein the medical diagnostic device further comprises a storage device connected to the medical diagnostic device, and the enabling system transmits information related to the consumable material required for executing the specific medical procedure and information related to a patient undergoing the specific medical procedure to the storage device.

4. The method according to claim 1, wherein the medical diagnostic device further comprises a display device, and the enabling system triggers a display of information related to the specific operating mode and to the consumable materials required for executing the medical procedure corresponding to the specific operating mode on the display device.

5. The method according to claim 1, wherein a transponder is assigned to the consumable material required for executing the medical procedure corresponding to the specific operating mode, and the reading device reads out the transponder for identifying the consumable materials.

6. The method according to claim 5, wherein the transponder includes an EEPROM, and the reading out of the transponder by means of the reading device includes a permanent modification of the memory contents of the EEPROM.

7. The method according to claim 1, wherein the medical diagnostic device further comprises a measuring and control unit for selecting one of the operating modes by a user.

* * * * *

UNITED STATES PATENT AND TRADEMARK OFFICE
CERTIFICATE OF CORRECTION

PATENT NO. : 7,664,658 B2
APPLICATION NO. : 11/089248
DATED : February 16, 2010
INVENTOR(S) : Harrison et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1310 days.

Signed and Sealed this

Thirtieth Day of November, 2010

David J. Kappos
*Director of the United States Patent and Trademark Office*